(12) United States Patent
Chavarria et al.

(10) Patent No.: US 9,398,928 B2
(45) Date of Patent: Jul. 26, 2016

(54) ADJUSTABLE HEIGHT ARTHROPLASTY PLATE

(71) Applicant: DEPUY SYNTHES PRODUCTS, INC., Raynham, MA (US)

(72) Inventors: Jason M Chavarria, Warsaw, IN (US); Scott A Lubensky, Winona Lake, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 344 days.

(21) Appl. No.: 13/834,802

(22) Filed: Mar. 15, 2013

(65) Prior Publication Data

US 2014/0094855 A1    Apr. 3, 2014

Related U.S. Application Data

(60) Provisional application No. 61/706,916, filed on Sep. 28, 2012.

(51) Int. Cl.
| | |
|---|---|
| *A61F 2/40* | (2006.01) |
| *A61B 17/80* | (2006.01) |
| *A61B 17/68* | (2006.01) |
| *A61B 17/88* | (2006.01) |
| *A61F 2/30* | (2006.01) |
| *A61B 17/74* | (2006.01) |

(52) U.S. Cl.
CPC ............. *A61B 17/8061* (2013.01); *A61B 17/68* (2013.01); *A61B 17/88* (2013.01); *A61F 2/40* (2013.01); *A61F 2/4014* (2013.01); *A61B 17/746* (2013.01); *A61F 2002/3055* (2013.01); *A61F 2002/30332* (2013.01); *A61F 2002/30405* (2013.01); *A61F 2002/30433* (2013.01); *A61F 2002/30474* (2013.01); *A61F 2002/30507* (2013.01); *A61F 2002/30578* (2013.01)

(58) Field of Classification Search
CPC ... A61F 2/3601; A61F 2/4003; A61F 2/4014; A61F 2002/30433; A61F 2002/30507; A61F 2002/30553; A61F 2/40; A61F 2/4684; A61B 17/8061; A61B 17/68; A61B 17/746; A61B 17/88
USPC ............................................. 623/19.11–19.14
See application file for complete search history.

(56) References Cited

U.S. PATENT DOCUMENTS

| 2,381,050 | A | * | 8/1945 | Hardinge | ............ A61B 17/742 411/55 |
|---|---|---|---|---|---|
| 2,397,545 | A | * | 4/1946 | Hardinge | ........................ 606/65 |
| 2,612,159 | A | * | 9/1952 | Collison | ........................ 606/67 |
| 3,374,786 | A | * | 3/1968 | Callender, Jr. | .................. 606/65 |
| 3,554,193 | A | * | 1/1971 | Konstantinou | ....... A61B 17/746 403/131 |

(Continued)

FOREIGN PATENT DOCUMENTS

| DE | 10123517 C1 | 11/2002 |
|---|---|---|
| DE | 102008053566 A1 | 6/2009 |

(Continued)

*Primary Examiner* — Alvin Stewart

(57) ABSTRACT

An orthopaedic assembly. The orthopaedic assembly includes a first member adapted to be coupled to a bone and an adjustable connector assembly including an adjuster having a threaded end and a tapered end. The assembly also includes an articulation component including a bearing surface and adapted to be coupled to the tapered end of the adjustable connector assembly. The threaded end is adapted to engage the fixation plate.

9 Claims, 6 Drawing Sheets

(56) References Cited

U.S. PATENT DOCUMENTS

| | | | | |
|---|---|---|---|---|
| 4,005,495 A * | 2/1977 | Locke et al. | | 623/23.14 |
| 4,045,825 A | 9/1977 | Stroot | | |
| 4,101,985 A * | 7/1978 | Baumann et al. | | 623/22.46 |
| 4,129,903 A * | 12/1978 | Huggler | | 623/23.11 |
| 4,438,762 A * | 3/1984 | Kyle | | 606/65 |
| 4,612,920 A * | 9/1986 | Lower | | 606/66 |
| 4,657,001 A * | 4/1987 | Fixel | | 606/66 |
| 4,686,971 A | 8/1987 | Harris | | |
| 4,776,329 A * | 10/1988 | Treharne | | 606/65 |
| 4,791,918 A * | 12/1988 | Von Hasselbach | | A61B 17/746 606/286 |
| 4,795,473 A * | 1/1989 | Grimes | | 623/23.11 |
| 4,904,264 A | 2/1990 | Scheunemann | | |
| 4,976,740 A * | 12/1990 | Kleiner | | 623/23.14 |
| 4,998,937 A * | 3/1991 | Grimes | | 606/89 |
| 5,087,260 A * | 2/1992 | Fixel | | 606/65 |
| 5,176,681 A * | 1/1993 | Lawes et al. | | 606/64 |
| 5,197,989 A | 3/1993 | Hinckfuss | | |
| 5,376,125 A * | 12/1994 | Winkler | | A61F 2/32 623/23.11 |
| 5,484,439 A * | 1/1996 | Olson et al. | | 606/65 |
| 5,514,138 A * | 5/1996 | McCarthy | | 606/65 |
| 5,569,263 A * | 10/1996 | Hein | | 606/102 |
| 5,645,607 A * | 7/1997 | Hickey | | 623/23.35 |
| 5,658,339 A * | 8/1997 | Tronzo | | A61B 17/746 606/65 |
| 5,725,593 A * | 3/1998 | Caracciolo | | 623/22.23 |
| 5,725,597 A | 3/1998 | Hwang | | |
| 5,733,292 A * | 3/1998 | Gustilo et al. | | 606/88 |
| 5,741,262 A * | 4/1998 | Albrektsson et al. | | 606/80 |
| 5,749,872 A * | 5/1998 | Kyle et al. | | 606/66 |
| 5,766,263 A * | 6/1998 | Grundei | | A61F 2/30907 623/23.15 |
| 5,800,553 A * | 9/1998 | Albrektsson | | A61B 17/1668 606/65 |
| 5,800,554 A * | 9/1998 | Scholz | | 623/22.43 |
| 5,800,557 A | 9/1998 | Elhami | | |
| 5,888,206 A * | 3/1999 | Lob et al. | | 623/18.11 |
| 5,980,575 A * | 11/1999 | Albrektsson et al. | | 623/23.11 |
| 6,010,535 A * | 1/2000 | Shah | | 623/22.16 |
| 6,139,552 A * | 10/2000 | Horiuchi | | A61B 17/748 606/65 |
| 6,221,074 B1 * | 4/2001 | Cole et al. | | 606/62 |
| 6,228,120 B1 | 5/2001 | Leonard | | |
| 6,270,499 B1 * | 8/2001 | Leu et al. | | 606/64 |
| 6,375,684 B1 * | 4/2002 | Kriek | | A61B 17/1666 623/23.39 |
| 6,383,227 B1 * | 5/2002 | Baroud et al. | | 623/23.22 |
| 6,402,753 B1 * | 6/2002 | Cole et al. | | 606/62 |
| 6,616,697 B2 * | 9/2003 | Sotereanos | | 623/23.26 |
| 6,706,073 B2 * | 3/2004 | Draenert et al. | | 623/22.46 |
| 7,097,663 B1 | 8/2006 | Nicol | | |
| 7,104,995 B2 * | 9/2006 | Crofford | | 606/81 |
| 7,135,023 B2 * | 11/2006 | Watkins | | A61B 17/748 606/65 |
| 7,156,879 B1 * | 1/2007 | Albrektsson et al. | | 623/23.14 |
| 7,247,171 B2 * | 7/2007 | Sotereanos | | 623/22.42 |
| 7,425,214 B1 * | 9/2008 | McCarthy et al. | | 606/89 |
| 7,569,075 B2 * | 8/2009 | Johnson et al. | | 623/22.41 |
| 7,695,474 B2 * | 4/2010 | Crofford | | 606/81 |
| 7,713,271 B2 * | 5/2010 | Warburton | | 606/64 |
| 7,753,961 B2 * | 7/2010 | Chen et al. | | 623/22.46 |
| 8,092,466 B2 * | 1/2012 | Splieth et al. | | 606/102 |
| 8,177,786 B2 * | 5/2012 | Leyden | | A61B 17/746 606/65 |
| 8,182,484 B2 * | 5/2012 | Grant et al. | | 606/66 |
| 8,187,276 B1 * | 5/2012 | Zahiri et al. | | 606/65 |
| 8,317,845 B2 * | 11/2012 | Stinnette | | 606/306 |
| 8,398,636 B2 * | 3/2013 | Simon et al. | | 606/65 |
| 8,460,393 B2 * | 6/2013 | Smith et al. | | 623/23.28 |
| 8,470,049 B2 * | 6/2013 | Walter et al. | | 623/23.15 |
| 8,506,641 B2 * | 8/2013 | Graham et al. | | 623/21.15 |
| 8,579,985 B2 * | 11/2013 | Podolsky et al. | | 623/22.42 |
| 8,679,121 B2 * | 3/2014 | Czartoski et al. | | 606/64 |
| 8,968,409 B2 * | 3/2015 | Chavarria et al. | | 623/18.11 |
| 2002/0107520 A1 * | 8/2002 | Hoffman | | A61B 17/15 623/23.11 |
| 2002/0143338 A1 * | 10/2002 | Orbay et al. | | 606/69 |
| 2002/0156474 A1 * | 10/2002 | Wack et al. | | 606/69 |
| 2002/0193797 A1 * | 12/2002 | Johnson et al. | | 606/79 |
| 2003/0028253 A1 | 2/2003 | Stone | | |
| 2003/0050704 A1 * | 3/2003 | Keynan | | 623/22.12 |
| 2003/0069582 A1 * | 4/2003 | Culbert | | A61B 17/68 606/65 |
| 2003/0187512 A1 | 10/2003 | Frederick | | |
| 2004/0162621 A1 * | 8/2004 | Crofford | | 623/22.43 |
| 2005/0197712 A1 | 9/2005 | Bigsby | | |
| 2006/0009852 A1 | 1/2006 | Winslow | | |
| 2006/0015101 A1 * | 1/2006 | Warburton et al. | | 606/62 |
| 2006/0116679 A1 * | 6/2006 | Lutz et al. | | 606/69 |
| 2006/0200249 A1 | 9/2006 | Beguin | | |
| 2006/0217720 A1 * | 9/2006 | Chieng | | A61F 2/32 606/65 |
| 2007/0038306 A1 * | 2/2007 | O'Gara | | 623/22.42 |
| 2007/0078519 A1 * | 4/2007 | Klotz | | 623/23.47 |
| 2007/0270847 A1 * | 11/2007 | Shaw | | 606/65 |
| 2008/0177395 A1 | 7/2008 | Stinnette | | |
| 2010/0023011 A1 * | 1/2010 | Nakamura | | A61B 17/746 606/64 |
| 2010/0023131 A1 | 1/2010 | Crofford | | |
| 2010/0249852 A1 * | 9/2010 | Brumfield et al. | | 606/282 |
| 2011/0066152 A1 * | 3/2011 | Keller | | A61B 17/725 606/62 |
| 2011/0196372 A1 * | 8/2011 | Murase | | 606/64 |
| 2011/0264233 A1 * | 10/2011 | Song | | 623/22.42 |
| 2011/0282395 A1 * | 11/2011 | Beyar et al. | | 606/301 |
| 2012/0109128 A1 * | 5/2012 | Frigg | | A61B 17/744 606/64 |
| 2013/0197652 A1 | 8/2013 | Ekelund | | |
| 2013/0338780 A1 * | 12/2013 | Berchoux et al. | | 623/19.11 |
| 2014/0094803 A1 * | 4/2014 | Overes | | A61B 17/74 606/66 |
| 2014/0094855 A1 * | 4/2014 | Chavarria et al. | | 606/281 |
| 2014/0114425 A1 * | 4/2014 | Ekelund et al. | | 623/19.14 |
| 2014/0121709 A1 * | 5/2014 | Gonzalez-Hernandez | | 606/286 |
| 2014/0121713 A1 * | 5/2014 | Meulink et al. | | 606/316 |
| 2014/0277520 A1 * | 9/2014 | Chavarria et al. | | 623/19.13 |
| 2014/0277521 A1 * | 9/2014 | Chavarria et al. | | 623/19.13 |

FOREIGN PATENT DOCUMENTS

| | | |
|---|---|---|
| FR | 2946863 A1 | 12/2010 |
| GB | 2007980 A | 5/1979 |
| JP | 2004089712 A | 3/2004 |
| WO | WO 8505027 A1 | 11/1985 |
| WO | WO 0009038 A2 | 2/2000 |
| WO | WO 2006126238 A2 | 11/2006 |
| WO | WO 2007024980 A2 | 3/2007 |
| WO | WO 2007082925 A2 | 7/2007 |
| WO | WO 2012104285 A1 | 8/2012 |
| WO | WO 2012130517 A1 | 10/2012 |

* cited by examiner

ADJUSTABLE HEIGHT ARTHROPLASTY PLATE

CROSS-REFERENCE TO RELATED APPLICATION

This application claims priority to U.S. Prov. App. No. 61/706,916 filed Sep. 28, 2012, entitled "Adjustable Height Arthroplasty Plate," which is incorporated by reference herein in its entirety.

TECHNICAL FIELD OF THE INVENTION

The present invention relates generally to the field of orthopedics, and, more particularly, to an arthroplasty plate for repairing fractures of an end of a long bone.

BACKGROUND

A natural shoulder joint may undergo degenerative changes for a variety of reasons, for instance arthritis. Alternatively, a shoulder joint may be fractured or otherwise damaged by an external force. When a shoulder joint is sufficiently degenerated or damaged it may be necessary to replace the natural joint with a prosthetic shoulder joint. Conventional shoulder prostheses comprise a humeral prosthesis, optionally with a glenoid prosthesis. For total or reverse arthroplasty a glenoid component is implanted, however for hemiarthroplasty the humeral component articulates against the natural glenoid cavity.

When the upper extremity of the humerus is fractured, the humerus generally breaks into several pieces, typically three or four. In particular, for a four part fracture, the humeral head splits off at the level of the anatomical neck, the greater and lesser tuberosities are separated from the humerus shaft below the tuberosities and the tuberosities are separated from one another along the bicipetal groove. As there is no longer a blood supply to the humeral head necrosis may begin. For repair of a three-part or four-part fracture, where the blood supply to the humeral head is damaged, the humeral head is replaced, and the greater and lesser tuberosities are reattached to the humeral shaft. Typically, the humeral component of a shoulder prosthesis comprises a stem for insertion into a bore extending into the intramedullary canal of the humerus, generally along the longitudinal axis of the bone, and an articulation component, which may be a convex bearing head in the case of total arthroplasty or a concave cup in the case of reverse arthroplasty. Typically, the articulation component is coupled to a neck portion of the stem, which extends from the intramedullary canal at an inclined angle relative to the longitudinal axis of a distal portion of the stem in order to recreate the anatomy of the natural joint. Commonly, humeral stem prostheses are secured in position within the intramedullary bore using bone cement. Alternatively, the stem may be coated with a material which encourages bone growth to hold the stem in position, such as Porocoat® or hydroxyapatite. One such humeral stem prosthesis is commercially available from DePuy Orthopaedics, Inc under the trademark Global FX.

As an alternative to humeral stem implants, it is known to repair some types of proximal humeral fracture using an intramedullary nail extending along a bore formed within the intramedullary canal. Screws pass from outside of the humerus, through holes formed within the nail and into the humeral head and the tuberosities. This type of fixation also suffers from vascular damage in the intramedullary canal. Furthermore, a significant drawback is that because the humeral head is not replaced the nail must be inserted through a hole formed in the articular cartilage of the humeral head. A plug must be inserted into the hole to restore the bearing surface.

For the repair of fractures of the femoral neck it is known to provide a form of prosthesis generally known as a thrust plate prosthesis. One such form of thrust plate prosthesis is disclosed within PCT patent publication WO2007/024980-A2. The prosthesis comprises a plate portion to be attached to the lateral external surface of the proximal femur.

One issue in dealing with long-limb arthroplasty, is accommodating various anatomic sizes. This becomes even more of a challenge when the desired sizes of linking components that must engage and disengage and be mechanically stable. Also, surgeons desiring the ability to adjust intra-operatively creates additional issues as does the desire by surgeons to have infinite adjustability, not finite size offerings.

It is an object of embodiments of the present invention to obviate or mitigate one or more of the problems of the prior art, whether identified herein or elsewhere.

SUMMARY OF THE INVENTION

According to one embodiment of the present invention, an orthopaedic assembly is provided. The assembly includes a first member adapted to be coupled to a bone and an adjustable connector assembly including an adjuster having a threaded end and a tapered end. The assembly further includes an articulation component including a bearing surface and adapted to be coupled to the tapered end of the adjustable connector assembly. The threaded end is adapted to engage the fixation plate.

According to another embodiment of the present invention, an arthroplasty plate is provided. The arthroplasty plate includes a fixation plate adapted to be fixed to a surface of a bone, having a recess with a plurality of tapers and an adjustable connector assembly including an adjuster having a plurality of tapers on a first end a taper on a second end. An articulation component is also included and has a bearing surface and adapted to be coupled to the tapered second end of the adjustable connector assembly. The plurality of tapers are adapted to engage at least one of the plurality of tapers in the recess of the fixation plate.

According to yet another embodiment of the present invention, a method of repairing a fractured end of a bone includes removing fractured portions of an articulating bone surface at the end of a bone. The method further includes securing a fixation plate to a lateral surface of the fractured end of the bone. The fixation plate is coupled to adjustable connector assembly, which includes an adjuster having a threaded end and a tapered end. The adjuster is threaded into or out of a threaded bore of the fixation plate to adjust the length of the adjuster extending from the bore of the fixation plate. The position of the adjuster is locked within the threaded bore.

DETAILED DESCRIPTION

Figure 1:
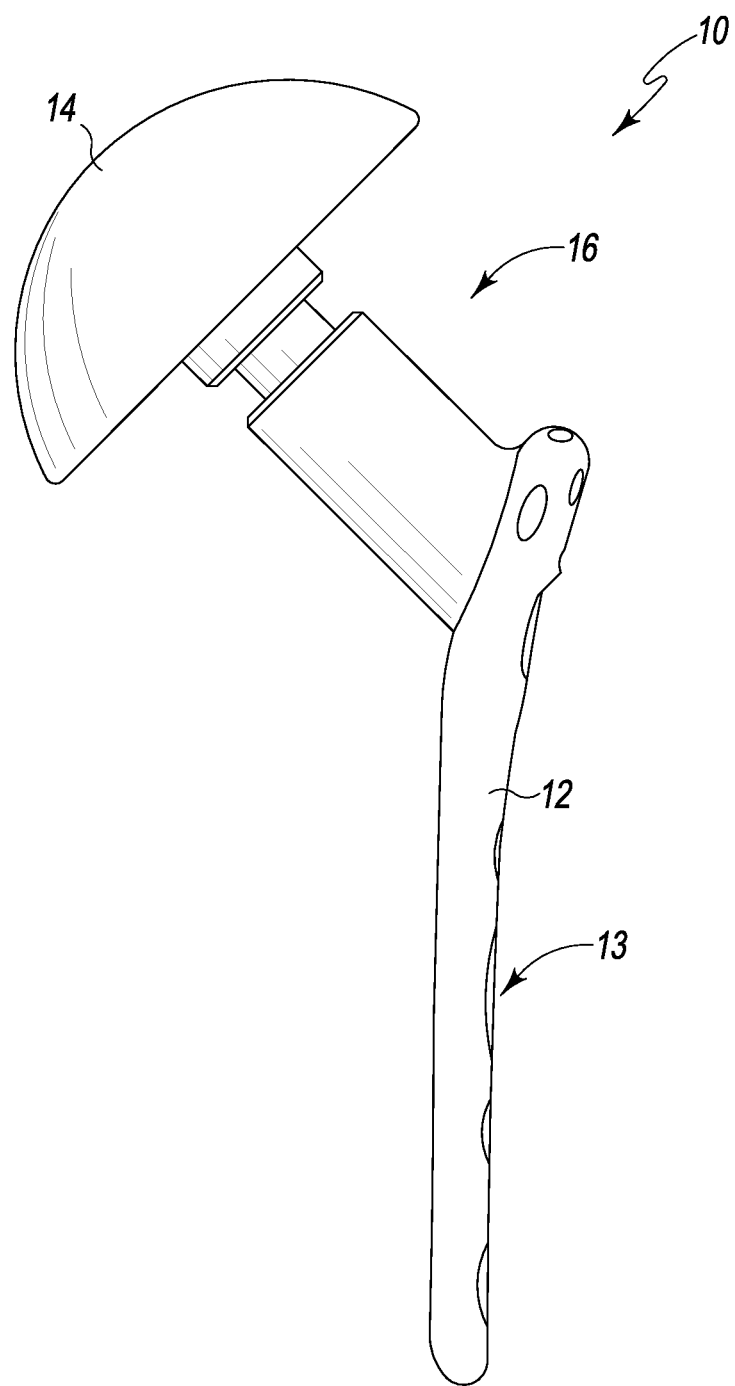
FIG. 1 is a view in a frontal plane of an arthroplasty plate according to an embodiment of the present invention.

Like reference numerals refer to like parts throughout the following description and the accompanying drawings.

The below description will be given with respect to a humeral prosthesis, and more particularly, a hemiarthroplasty plate. However, it should be understood that the present invention may be used in other types of prosthesis and that the hemiarthroplasty plate is used as an example only. For example, instead of a fixation plate, a stem or other arthroplasty component could be used. And, any articulation member, not just humeral heads could be used as well.

Referring first to FIG. 1, this is a view in a frontal plane of an assembled arthroplasty plate 10 for repair of a fractured proximal humerus in accordance with an embodiment of the present invention. The arthroplasty plate comprises a fixation plate (or first member of an orthopaedic assembly) 12 for attachment to a surface of the bone, in this case, a lateral external portion of a proximal humerus of a patient. To aid in the fixation to the bone, the fixation plate 12 may include a plurality of fixation holes 13 adapted to receive bone screws (not shown). An articulation component 14 replaces the natural humeral head. The articulation component 14 comprises a convex bearing surface and is sized and shaped to articulate with either the natural glenoid surface or an implanted glenoid prosthesis to reconstruct the shoulder joint. The articulation component 14 is coupled to the fixation plate 12 via a connector assembly 16 positioned in a bore formed in the proximal humerus.

Figure 2:
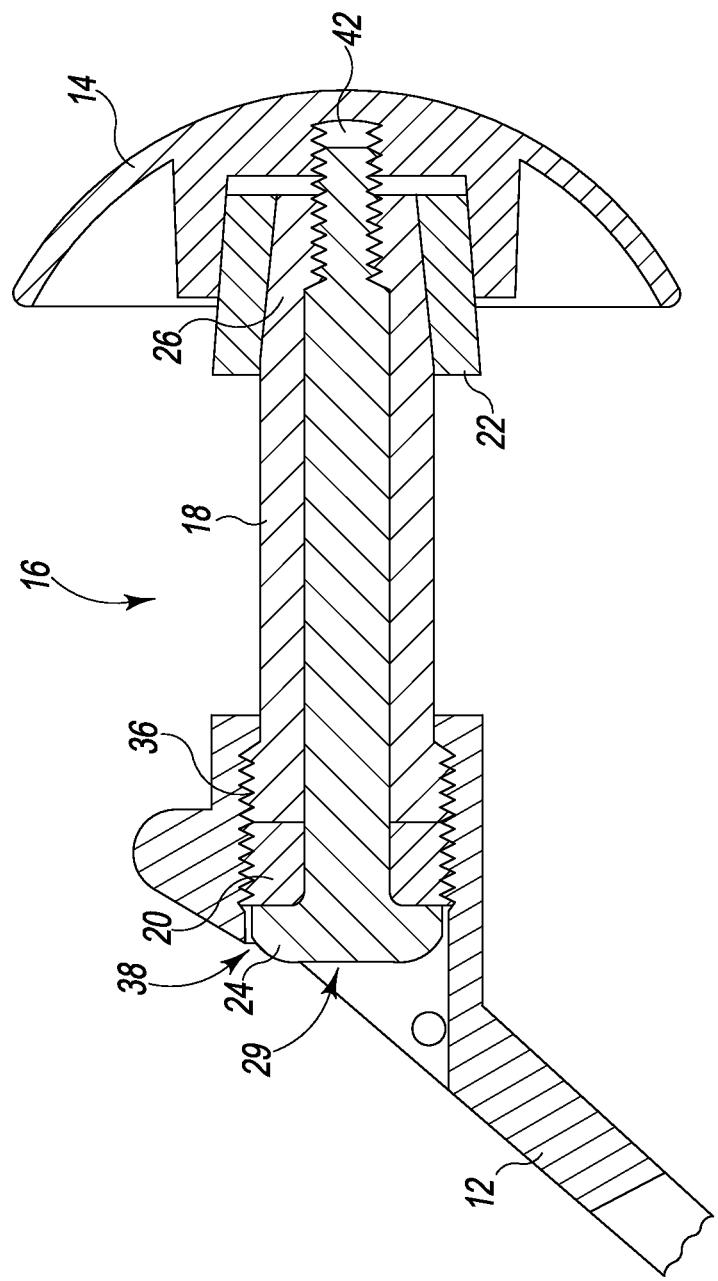
FIG. 2 is a cross-sectional view of the arthroplasty plate of FIG. 1.
Figure 4:
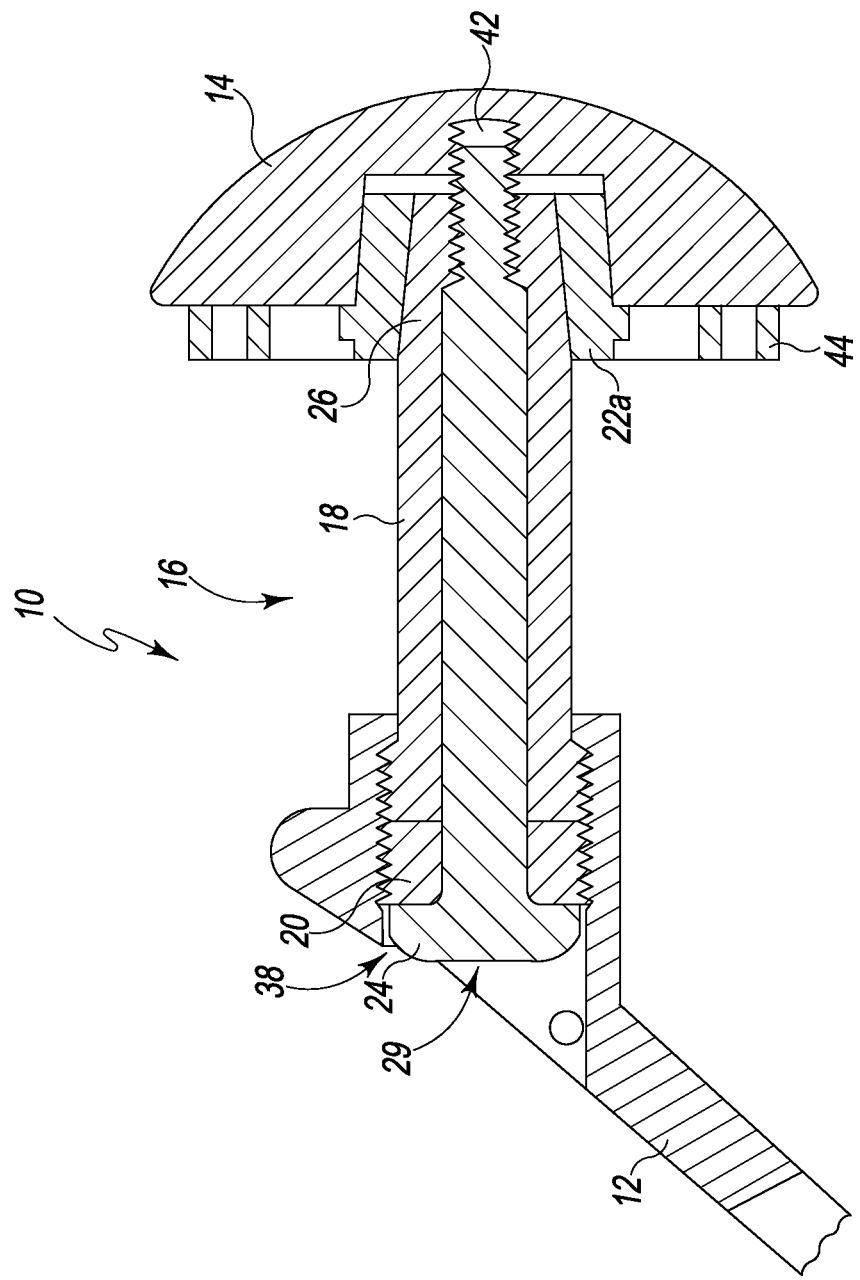
FIG. 4 is a cross-sectional view of an arthroplasty plate according to another embodiment of the present invention.

Referring now to FIG. 2, this illustrates a cross sectional view of the connector assembly of the arthroplasty plate of FIG. 1 to better illustrate details of the connector assembly 16. In this embodiment, the connector assembly 16 is an adjustable assembly to allow the user to adjust the neck length of the arthroplasty plate 10. The adjustable connector assembly 16 includes an adjuster 18, a locking screw 20, collar 22, and assembly screw 24. The collar 22 is used as a placeholder or substitute for the larger suture collar (FIG. 4).

Figure 3:
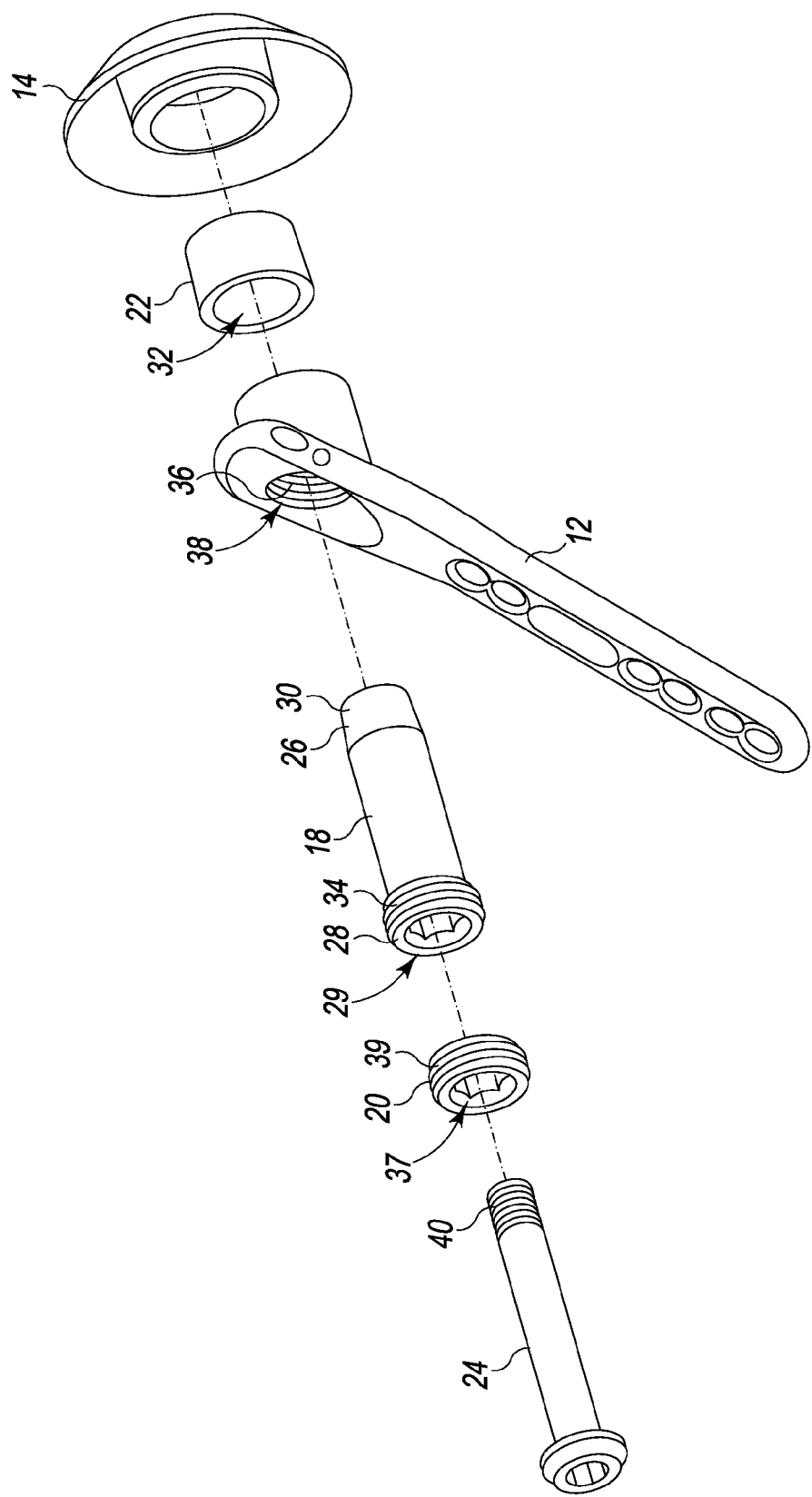
FIG. 3 is an exploded view of the arthroplasty plate according to FIG. 1.

Referring to both FIGS. 2 and 3, the various features of the adjustable connector assembly 16 will be further described. The adjuster 18 includes a first end 26 and a second end 28. The first end 26 includes a connection feature 30 adapted to couple to a corresponding connection feature 32 of the collar 22. In the illustrated embodiment, the connection feature 30 of the first end 26 is a male taper and the connection feature 32 of the collar 22 is a female taper. According to some embodiments, the male and female tapers are locking tapers, adapted to lock the adjuster 18 to the collar 22. In some embodiments, the adjuster 18 may lock directly into the articulation component 14. In those embodiments, the connection feature 30 of the first end 26 of the adjuster 18 is a male taper and is adapted to fit into a corresponding tapered recess in the articulation component 14. The adjuster 18 also includes a through bore 29 extending between the first end 26 and the second end 28.

The second end 28 of the adjuster 18 includes a connection feature 34 adapted to connect to a corresponding connection feature 36 in the fixation plate 12. In the illustrated embodiments of FIGS. 2 and 3, the connection feature 34 of the second end 28 is a thread and the connection feature 36 in the fixation plate 12 is a corresponding thread form. In use, the adjuster 18 is inserted into through bore 38 in the fixation plate 12. As shown, the through bore 38 is threaded so as to engage the threads of the connection feature 34 of the second end 28. Once the adjuster 18 is at the desired length, the locking screw 20 is screwed into the connection feature 36 of the fixation plate 12, locking the adjuster 18 into place. In order to lock the adjuster 18 into place, the locking screw 20 includes a bore 37 and external threads 39. The external threads 39 of the locking screw 20 engage the threaded through bore 38 of the fixation plate 12, as shown in FIG. 2. The adjuster 18 and the locking screw 20 are locked relative to each other and to the fixation plate 12 on the principal of a locking nut. The adjuster thread 34 is in contact with the top flank of the threads of feature 36 of the plate 12 and the locking screw thread 39 is in contact with the opposite or bottom flank of the threads of the plate 12, making relative movement not possible. The collar 22 is then placed over the first end 26 of the adjuster 18. The tapered connection feature 32 of the collar 22 is then locked into place with the tapered connection feature 30 of the first end 26 of the adjuster 18. The articulation component 14 may then be placed onto the collar 22.

The assembly screw 24 includes a threaded end 40 and the articulation component 14 includes a corresponding threaded opening 42 (shown in FIG. 2). After the articulation component 14 is placed onto the collar 22, the assembly screw 24 is inserted through the bores 37, 29, 38 of the locking screw 20, adjuster 18, and fixation plate, respectively. The threaded end 40 of the assembly screw 24 then threads into the threads of the threaded opening 42 of the articulation component 14, locking all of the pieces together.

Figure 5:
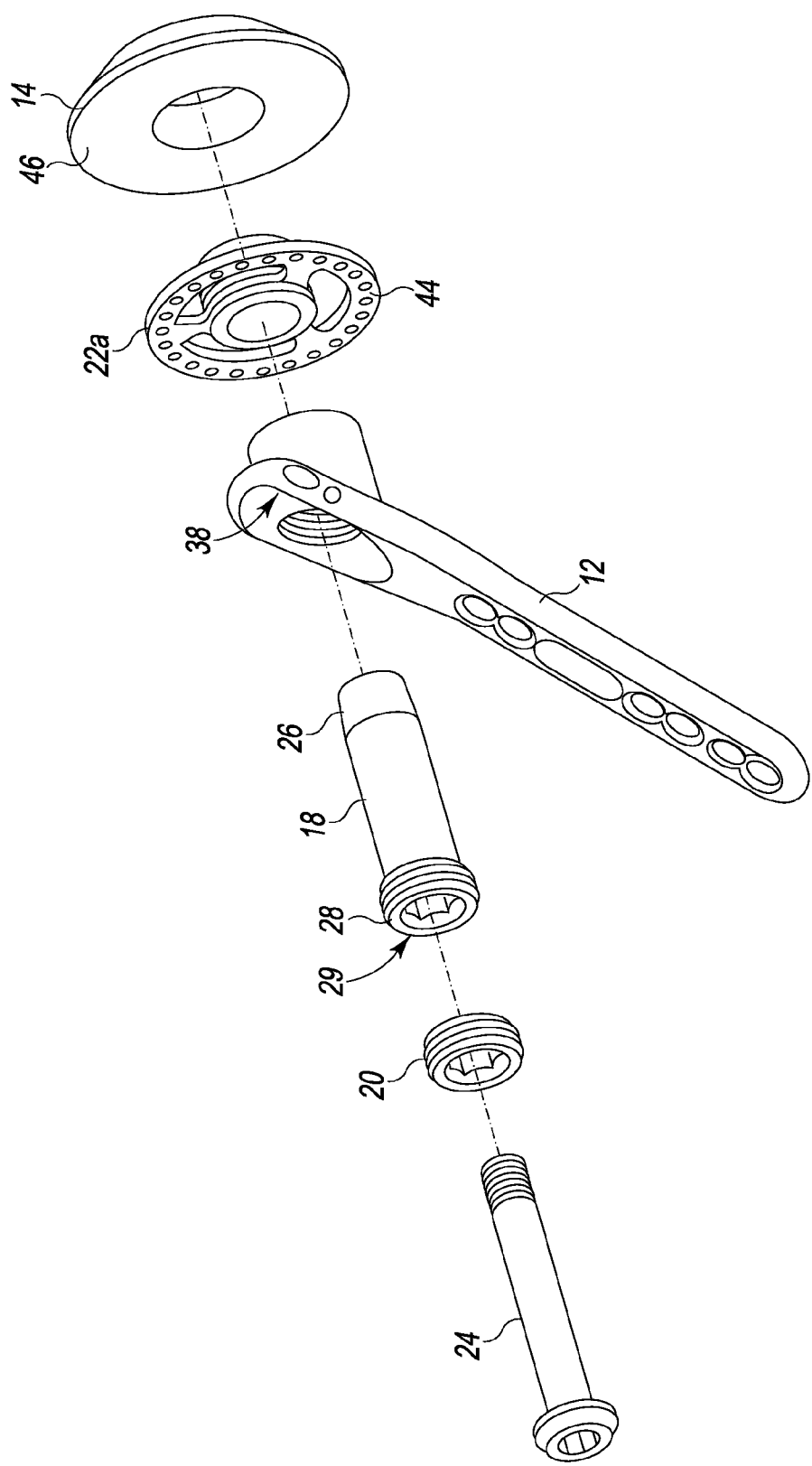
FIG. 5 is an exploded view of the arthroplasty plate of FIG. 4.

Turning now to FIGS. 4 and 5, another embodiment of the present invention is illustrated. As shown, the arthroplasty plate assembly 10 includes a fixation plate 12, articulation component 14, an assembly screw 24, a locking screw 20, an adjuster 18, and a collar 22a. In this embodiment, all the features are the same, with the exception that the collar 22a is a plate, having a flange 44 that extends outwardly and abuts an outwardly extending flange 46 (of FIG. 5) of the articulation component 14.

Figure 7:
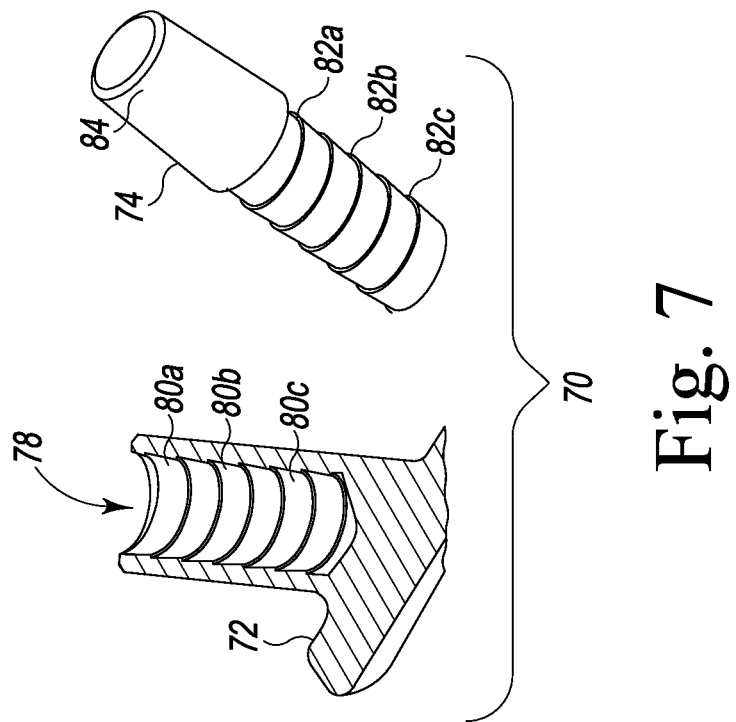
FIG. 7 is an exploded view of the arthroplasty plate of FIG. 6.
Figure 6:
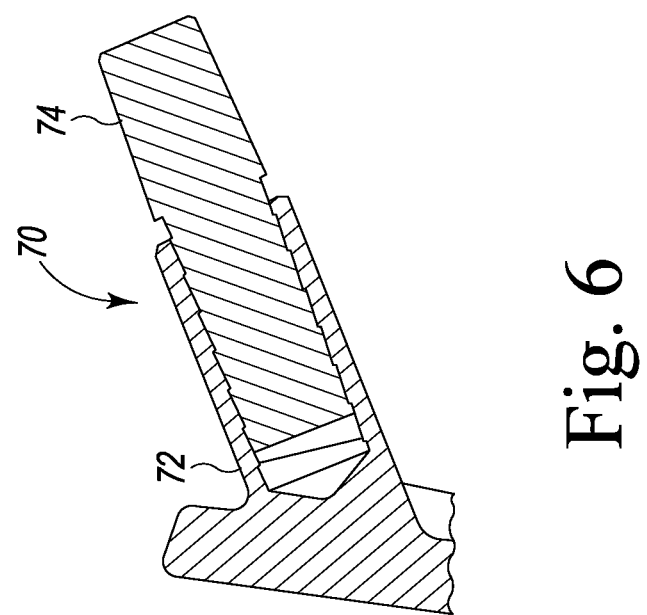
FIG. 6 is a cross-sectional view of an arthroplasty plate according to another embodiment of the present invention.

Turning now to FIGS. 6 and 7, another embodiment of the present invention is illustrated. This embodiment is of an arthroplasty plate 70 having a fixation plate 72, an adjustable connector 74, and an articulation component 14 (of FIG. 1). In this embodiment, the fixation plate 72 includes a through bore 78 that has a thread form that creates series of tapers 80a, 80b, 80c. As illustrated, the thread form is a continuous thread, but in other embodiments in can be discontinuous. In this embodiment, the adjustable connector 74 is the adjuster and includes a plurality of corresponding tapers 82a, 82b, 82c. The user would insert the adjustable connector 74 into the through bore 78 of the fixation plate 72 and, once at the appropriate length, impacted to engage the tapers 80a, 82a to lock the adjuster 74 into place in the fixation plate 72. In some embodiments, multiple tapers would engage at the appropriate length. At the other end of the adjuster is a male taper 84. The male taper 84 is adapted to fit inside a female taper (not shown) of the articulation component 14 (of FIG. 1). The articulation component 14 is then impacted onto the adjuster 74, locking the tapers 84. In some embodiments, an assembly screw can be used.

The foregoing description of the invention is illustrative only, and is not intended to limit the scope of the invention to the precise terms set forth. Further, although the invention has been described in detail with reference to certain illustrative embodiments, variations and modifications exist within the scope and spirit of the invention as described and defined in the following claims.

What is claimed is:

1. An arthroplasty plate comprising:
   a fixation plate adapted to be fixed to a surface of a bone, having a recess with a plurality of tapers;
   an adjustable connector assembly including an adjuster having a plurality of tapers on a first end a taper on a second end; and
   an articulation component including a bearing surface and adapted to be coupled to the tapered second end of the adjustable connector assembly;
   wherein the plurality of tapers are adapted to engage at least one of the plurality of tapers in the recess of the fixation plate.

2. The arthroplasty plate of claim 1, wherein the fixation plate includes a plurality of fixation through holes adapted to receive bone screws.

3. The arthroplasty plate of claim 1, wherein the fixation plate is adapted to be fixed onto a humerus.

4. The arthroplasty plate of claim 1, wherein the articulation component is adapted to engage a glenoid.

5. A method of repairing a fractured end of a bone, the method comprising:
   removing fractured portions of an articulating bone surface at the end of a bone;
   securing a fixation plate to a lateral surface of the fractured end of the bone, the fixation plate being coupled to an adjustable connector assembly including an adjuster having a threaded end and a tapered end;
   coupling an articulation component to the tapered end of the adjuster wherein the coupling an articulation component to the tapered end of the adjuster includes inserting a collar over the tapered end of the adjuster and inserting the articulation component onto an outer side of the collar;
   threading the adjuster into or out of a threaded bore of the fixation plate to adjust the length of the adjuster extending from the bore of the fixation plate; and
   locking the position of the adjuster within the threaded bore.

6. The method of claim 5, wherein locking the position of the adjuster within the threaded bore includes threading a locking screw into the threaded bore.

7. The method of claim 6, further comprising inserting an assembly screw through the locking screw and the adjuster.

8. The method of claim 7, wherein the inserting an assembly screw includes inserting a threaded end of the assembly screw through the locking screw and the adjuster.

9. The method of claim 8, further comprising threading the threaded end of the assembly screw into a threaded recess of the articulation component.

\* \* \* \* \*